United States Patent [19]

Ishikawa et al.

[11] Patent Number: 4,605,615
[45] Date of Patent: Aug. 12, 1986

[54] L-GLUTAMIC ACID OXIDASE ($H_2O_2$-GENERATING), ITS PRODUCTION AND ANALYTICAL METHOD THEREFOR

[75] Inventors: Hidehiko Ishikawa; Hideo Misaki; Naoki Muto, all of Shizuoka, Japan

[73] Assignee: Toyo Jozo Kabushiki Kaisha, Shizuoka, Japan

[21] Appl. No.: 472,174

[22] Filed: Mar. 2, 1983

[30] Foreign Application Priority Data

Mar. 2, 1982 [JP] Japan .................. 57-33497

[51] Int. Cl.[4] .................. C12Q 1/52; C12Q 1/36; C12Q 1/26; C12N 9/06; C12R 1/465
[52] U.S. Cl. .................. 435/16; 435/24; 435/25; 435/191; 435/886
[58] Field of Search .................. 435/25, 189, 191, 24, 435/16

[56] References Cited

FOREIGN PATENT DOCUMENTS 57-43685 3/1982 Japan .................. 435/191

*Primary Examiner*—Lionel M. Shapiro
*Attorney, Agent, or Firm*—Young & Thompson

[57] ABSTRACT

L-glutamic acid oxidase having the following biochemical properties:
(a) substrate specificity: L-glutamic acid,
(b) enzyme action: catalyzes a reaction which forms one mole of α-ketoglutaric acid, one mole of ammonia and one mole of hydrogen peroxide from one mole of L-glutamic acid, one mole of oxygen and one mole of water, as follows:

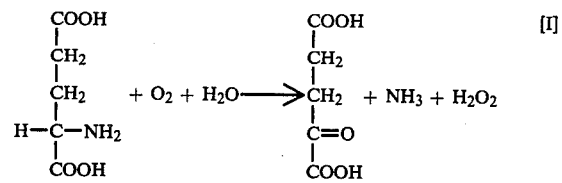

This oxidase is produced by culturing microorganisms belonging to genus Streptomyces in a nutrient medium and isolating the thus-produced L-glutamic acid oxidase. Particular microorganisms of genus Streptomyces are sp. A7700 FERM P-6241 (NRRL No. 15267) and sp. 8063 FERM P-6242 (NRRL No. 15268). The oxidase can be used for detecting L-glutamic acid or L-glutamate, in an aqueous sample, because it catalyzes a reaction which forms one mole of α-ketoglutaric acid, one mole of ammonia and one mole of hydrogen peroxide from one mole of glutamic acid, one mole of oxygen and one mole of water. Thus, the consumed oxygen can be quantitatively determined, or the generated α-glutaric acid or ammonia or hydrogen peroxide can be quantitatively determined.

14 Claims, 12 Drawing Figures

L-GLUTAMIC ACID OXIDASE (H₂O₂-GENERATING), ITS PRODUCTION AND ANALYTICAL METHOD THEREFOR

This invention relates to L-glutamic acid oxidase having substrate specificity for L-glutamic acid or L-glutamate and an enzymatic action catalyzing a reaction which forms one mole of α-ketoglutaric acid, one mole of ammonia and one mole of hydrogen peroxide from one mole of L-glutamic acid, one mole of oxygen and one mole of water. The invention also relates to a process for the production of such L-glutamic acid oxidase, and an analytical method using such L-glutamic acid oxidase.

The only hitherto-known oxidase having substrate specificity for L-glutamic acid is L-(+)-glutamate oxidoreductase having an enzymatic action catalyzing a reaction which forms two moles of α-ketoglutaric acid, two moles of ammonia and one mole of water from two moles of L-glutamic acid, one mole of oxygen and one mole of water. [*Biochim. Biophys. Acta*, 368, 158–172 (1974)].

Furthermore, there is also known an L-amino acid oxidase having substrate specificity for L-amino acid and an enzymatic action catalyzing a reaction which forms one mole of α-keto acid, one mole of ammonia and one mole of hydrogen peroxide from one mole of amino acid, one mole of oxygen and one mole of water. [*Methods in Enzymology*, Vol. II, 204–211 (1955) and others].

In this prior art, L-(+)-glutamate oxidoreductase catalyzes the reaction hereinabove set forth and does not produce hydrogen peroxide. Furthermore, L-amino acid oxidase is an enzyme which catalyzes a reaction as above explained and hence hydrogen peroxide is produced. However, among the prior known L-amino acid oxidases, no enzyme which acts on a substrate comprising L-glutamic acid has been reported. [*Methods in Enzymology*, Vol. II, p. 204–211 (1955)].

We have found that Streptomyces strain A7700 isolated from a soil sample from a field in Saku-shi, Nagano-ken, Japan, and Streptomyces strain A8063 isolated from a soil sample from a sweet potato field in Naganohara-cho, Azuma-gun, Gunma-ken, Japan, produce an enzyme having substrate specificity for L-glutamic acid and catalyzing a reaction which forms one mole of α-ketoglutaric acid, one mole of ammonia and one mole of hydrogen peroxide from one mole of L-glutamic acid, one mole of oxygen and one mole of water; and we have purified the said enzyme as a single protein. We have designated the said enzyme as L-glutamic acid oxidase. Also we have discovered a novel analysis method for a liquid sample containing L-glutamic acid by using this novel enzyme.

The taxonomical properties of the Streptomyces strains A7700 and A8063 are as follows:

(A) Streptomyces strain A7700:

I. Microscopic observations

Morphological observations upon culturing on starch-inorganic salt agar medium at 30° C. for 10–15 days are as follows: (Almost the same observations were made when using oatmeal agar medium and yeast extract-malt extract agar medium.)

The substrate mycelia are curved, grown with branching, 0.5–0.6μ in diameter and have no mycelial oidium and are not spore bearing.

The aerial mycelia grown on substrate mycelia are curved, grown with simple branchings, 0.6–0.8μ in diameter and form many chain spores. Spore chains are spiral with 2–3 rounds and sometimes looped or hooked.

The spores are elliptical or short rods and 0.6–0.8×0.8–1.0μ in size with smooth surfaces.

No flagellar spores or sporangia are formed.

II. Composition of diaminopimelic acid

L-diaminopimelic acid is found and no meso-type is detected in the whole cell analysis.

III. Macroscopic observation

Observations on various media at 30° C. for 14 days are shown in Table 1.

Color indicates are made by consulting the "Color Harmony Manual", 4th Ed., 1958 (Container Corp. of America).

IV. Physiological properties (1) Growth temperature: 20°–40° C.
(2) Oxygen requirement: aerobic.
(3) Gelatin liquefaction: positive (very weak).
(4) Starch hydrolysis: positive.
(5) Skim milk: peptonization: positive (weak), coagulation: negative.
(6) Melanine pigment formation: tyrosine agar: negative, peptone-yeast extract-iron agar: positive.
(7) Utilization of carbon sources:
   Positive: L-arabinose, D-fructose, D-glucose, inositol, D-mannitol, raffinose, L-rhamnose, sucrose and D-xylose.

TABLE 1

| Medium | Growth | Color of substrate mycelium | Aerial mycelium | Soluble pigment |
|---|---|---|---|---|
| Sucrose-nitrate agar | good | cinnamon (3le) | poor: pearl (3ba) to shell pink (5ba) | rust tan (5le) |
| Glucose-asparagine agar | moderate | light ivory (2ca) | none | none |
| Glycerol-asparagine agar | good | topaz (3ne) | moderate: white (a) to pearl (3ba) | none |
| Starch-inorganic salt agar | good | topaz (3ne) to cinnamon (3le) | moderate to good: pearl (3ba) | none |
| Tyrosine agar | good | cinnamon (3le) | moderate: pearl (3ba) | none |
| Oatmeal agar | moderate | bamboo (2fb) | modrate: white (a) to pearl (3ba) | none |
| Yeast extract-malt extract agar | good | light amber (3ic) to cinnamon (3le) | moderate to good: pearl (3ba) | none |
| Bennett's agar | good | adobe brown (3lg) | moderate: pearl (3ba) | topaz (3ne) |
| Emerson's agar | good | cinnamon (3le) | poor: white (a) to pearl (3ba) | light amber (3ic) |
| Nutrient agar | moderate to poor | light amber (3ic) | few: white (a) | none |
| Peptone-yeast extract-iron agar | moderate to poor | colorless | none | golden brown (3pi) to oak |

TABLE 1-continued

| Medium | Growth | Color of substrate mycelium | Aerial mycelium | Soluble pigment |
| --- | --- | --- | --- | --- |
|  |  |  |  | brown (4pi) |

As shown hereinabove, the strain A7700 has the taxonomical properties of forming aerial mycelia with many spore chains from true substrate mycelia, L-type diaminopimelic acid, no formation of flagellar spores or sporangia, and aerobic growth, and is thus identified as belonging to genus Streptomyces. This strain is referred as Streptomyces sp. A7700, and has been deposited in the Fermentation Institute, Agency of Industrial Science and Technology, M.I.T.I., Japan, as deposit No. FERM P-6241.

Also this strain has been deposited in the United States Agricultural Research Service, as deposit NRRL No. 15267.

(B) Streptomyces strain A8063:

I. Microscopic observations

Morphological observations upon culturing on starch-inorganic salt agar at 30° C. for 10–15 days are as follows: (Almost the same results are observed on glycerol-asparagin agar, tyrosine agar and yeast extract-malt extract agar medium.)

Substrate mycelia are curved and grown with branchings, $0.5-0.6\mu$ in diameter, and have no mycelial oidia or spore bearings.

Aerial mycelia grown on substrate mycelia are curved grown with simple branchings, $0.6-0.8\mu$ in diameter and have many chain spores.

The spore chains are abundant with loops, hooks or double spirals, and a few have triple or more spirals.

The spores are globose and $0.6-0.8\mu$ in diameter with spiny surfaces. No formation of flagellar spores or sporangia is noted.

II. Composition of diaminopimelic acid

L-diaminopimelic acid is found and no meso-type is detected in the whole cell analysis.

III. Macroscopic observation

Observations on various media at 30° C. for 14 days are shown in Table 2. Color indicates are made consulting the "Color Harmony Manual", 4th Ed., 1958.

IV. Physiological properties (1) Growth temperature: 15°–43° C.
(2) Oxygen requirement: aerobic.
(3) Gelatin liquefaction: positive (weak).
(4) Starch hydrolysis: positive.
(5) Skim milk: peptonization: positive, coagulation: negative.
(6) Melanin-like pigment formation: tyrosin agar medium and peptone-yeast extract-iron agar medium: positive.
(7) Utilization of carbon sources:
  Positive: D-fructose, D-glucose, D-mannitol, L-rhamnose and sucrose.
  Weakly positive: L-arabinose, inositol, raffinose and D-xylose.

As shown hereinabove, the strain A8063 has the taxonomical properties of forming aerial mycelia with many spore chains from true substrate mycelia; L-type diaminopimelic acid, no formation of flaggelar spores or sporangia, and aerobic growth, and is thus determined to belong to genus Streptomyces. This strain is referred as Streptomyces sp. A8063, and has been deposited in the Fermentation Institute, Agency of Industrial Science and Technology, M.I.T.I., Japan, as deposit No. FERM P-6242.

This strain has also been deposited in the United States Agricultural Research Service, as deposit NRRL No. 15268.

TABLE 2

| Medium | Growth | Color of substrate mycelium | Aerial mycelium | Soluble pigment |
| --- | --- | --- | --- | --- |
| Sucrose-nitrate agar | good | chocolate brown (5pn) | good: silver gray (3fe) to beige (3ge) | copper brown (5pi) to deep brown (5pl) |
| Glucose-asparagine agar | poor | dark spice brown (4pl) | few: natural (3dc) | oak brown (4pi) |
| Glycerol-asparagine agar | good | dark spice brown (4pl) to chocolate brown (4pn) | good: bisque (3ec) to beige (3ge) | oak brown (4pi) oak brown (4pi) |
| Starch-inorganic salt agar | good | dark spice brown (4pl) | good: silver gray (3fe) to beige (3ge) | none |
| Tyrosine agar | good | chocolate brown (5pn) | good: bisque (3ec) to beige (3ge) | copper brown (5pi) to deep brown (5pl) |
| Oatmeal agar | moderate | camel (3ie) to adobe brown (3lg) | good: bisque (3ec) to | None |
| Yeast extract-malt extract agar | good | dark spice brown (4pl) to chocolate brown (4pn) | good: bisque (3ec) to beige (3ge) | oak brown (4pi) |
| Bennett's agar | good | chocolate brown (4pn) to dark spice brown (4pl) | good: bisque (3ec) to beige (3ge) | oak brown (4pi) |
| Emerson's agar | moderate | oak brown (4pi) | poor: oyster white (b) | oak brown (4pi) |
| Nutrient agar | poor | cinnamon (3le) | few: white (a) | cinnamon (3le) |

The novel enzyme L-glutamic acid oxidase of the present invention is an enzyme catalyzing a reaction which forms one mole of α-ketoglutaric acid, one mole of ammonia and one mole of hydrogen peroxide from one mole of L-glutamic acid, one mole of oxygen and one mole of water. We have also discovered a method for detecting and/or quantifying L-glutamic acid in a sample containing L-glutamic acid by contacting a liquid sample containing L-glutamic acid with L-glutamic acid oxidase, and quantitatively measuring consumed oxygen, or generated hydrogen peroxide, ammonia or α-ketoglutarate corresponding to the amount of L-glutamate in this enzymatic reaction system.

An object of the present invention is to provide a novel enzyme L-glutamic acid oxidase having at least the following biochemical properties:

Substrate specificity: L-glutamic acid;

Enzyme action: catalyzing a reaction, which forms one mole of α-ketoglutaric acid, one mole of ammonia and one mole of hydrogen peroxide from one mole of L-glutamic acid, one mole of oxygen and one mole of water, as follows:

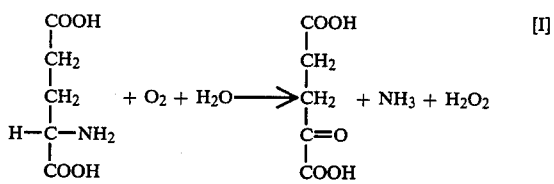

Another object of the present invention is to provide a process for production of L-glutamic acid oxidase which comprises culturing L-glutamic acid oxidase producing microorganisms belonging to genus Streptomyces in a nutrient medium and isolating the thus-produced L-glutamic acid oxidase.

A further object of the present invention is to provide an assay method for L-glutamic acid which comprises contacting a liquid sample containing L-glutamic acid with L-glutamic acid oxidase having substrate specificity for L-glutamic acid and catalyzing a reaction which generates one mole of α-ketoglutaric acid, one mole of ammonia and one mole of hydrogen peroxide from one mole of L-glutamic acid, one mole of oxygen and one mole of water, and quantitatively determining consumed oxygen or generated α-ketoglutaric acid, ammonia or hydrogen peroxide.

The novel L-glutamic acid oxidase of the present invention is sufficiently characterized by the substrate specificity and enzymatic action hereinbefore, and any enzymes having the same characteristics but different properties such as isoelectric point, Km value, optimum pH, heat stability, pH-stability and inhibition or activation additives, should naturally be included in the present invention.

The microorganisms specified hereinbefore are merely illustrative of microorganisms which produce the novel L-glutatmic acid oxidase, and other L-glutamic acid oxidase producing microorganisms belonging to genus Streptomyces can be included among the microorganisms used in the present invention. Generally speaking, microorganism strains are easily mutated naturally or artifically, and hence these mutants which have L-glutamic acid oxidase producing activity can be used in the present invention. Furthermore, strains which have been improved by recombinant DNA technology for the said enzyme production are also included in the present invention.

Figure 1:
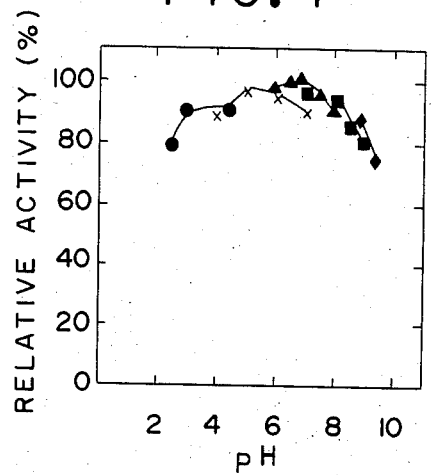
FIG. 1 is the optimum pH curve for the A7700 enzyme.

An embodiment of the process for the production of L-glutamic acid oxidase by the said enzyme producing microorganisms belonging to genus Streptomyces is as follows:

L-glutamic acid oxidase producing microorganisms belonging to genus Streptomyces are conventionally cultured in a nutrient medium for antibiotics or enzymes production. Solid or liquid culture can be used; however, submerged aeration culture is preferable for industrial production of the enzyme.

The nutrient sources for the microorganisms are conventional media for microorganism cultivation. As nitrogen sources, assimilable nitrogen sources, for example, corn steep liquor, soy bean powder, peptone, various meat extracts, yeast extracts, ammonium sulfate, ammonium chloride or amino acids such as L-glutamic acid can be used. As carbon sources, assimilable carbon sources such as sucrose, glucose, fructose, molasses, malt extract or starch hydrolyzate can be used. Furthermore, various inorganic salts such as sodium chloride, potassium chloride, magnesium sulfate, potassium phosphate or potassium dihydrogenphosphate, or antifoam agents can optionally be used.

The culturing temperature can be varied within the ranges of L-glutamic acid oxidase production and microorganism growth, and is usually 20°–35° C., preferably about 26° C.

The culturing time can be varied according to conditions, and is usually 50–120 hours, and the cultivation should naturally be terminated at the time of maximum production of enzyme.

L-glutamic acid oxidase of the present invention is an endo-enzyme and is included in the cells.

L-glutamic acid oxidase of the present invention can be isolated by separating the cultured cells from the cultured broth, suspending the wet cells in a buffer solution such as phosphate buffer, Tris-HCl buffer or dimethylglutarate-NaOH buffer, and treating by means of a French press, ultrasonication, a grinding mill treatment or a lysozyme treatment to obtain a crude solution of L-glutamic acid oxidase. The solution is further treated by known isolation and purification methods for proteins and enzymes to obtain purified L-glutamic acid oxidase. For example, the enzyme solution is subjected to organic solvent precipitation by adding an organic solvent such as acetone, methanol, ethanol or isopropanol, or salting-out by adding ammonium sulfate, and chromatography using an ion-exchanger such as diethylaminoethyl cellulose or diethylaminoethyl Sepharose, gel filtration chromatography using dextran gel or polyacrylamide gel. A purified enzyme powder can be obtained by combining the above procedures and finally lyophilizing the enzyme solution.

The assay method and biochemical properties of L-glutamic acid oxidase of the present invention are as follows:

1. Assay method:

| | |
|---|---|
| 0.3% 4-aminoantipyrine | 0.3 ml |
| peroxidase (50 U/ml) | 0.1 ml |
| 0.2 M phosphate buffer (pH) | 6 ml |
| 0.2% N,N—dimethyl-m-toluidine | ml |
| 0.2 M L-glutamic acid (pH 7.0) | 1.5 ml |
| distilled water | 0.2 ml |
| Total | 3.0 ml |

The above mixture (3.0 ml) was introduced into a quartz cell at 37° C., to which was immediately added and mixed the enzyme solution (50 μl), in a constant temperature (37° C.) cell-holder of a spectrophotometer. Then the mixture was incubated for exactly 5 minutes after 2 minutes of mixing with the enzyme solution, and the variation of absorption (optical density $\Delta A_{545}$) at 545 nm is measured.

The activity of the enzyme is calculated by the following equation:

L-glutamic acid oxidase activity (unit/ml) =

$$\frac{\Delta A_{545}}{32 \times \frac{1}{2}} \times \frac{1}{5} \times \frac{3.05}{0.05} \times \text{dilution ratio}$$

2. Substrate specificity:

The relative activities (%) of enzyme L-glutamic acid oxidases produced by Streptomyces sp. A7700 (hereinafter designated as A7700 enzyme) and by Streptomyces sp. A8063 (hereinafter designated as A8063 enzyme), respectively, on various substrates as compared with L-glutamic acid, are measured.

The results are shown in Table 3. Both enzymes have specific activity on L-glutamic acid and have no activity on the other amino acids as shown in the table.

TABLE 3

| Substrate | A7700 enzyme | A8063 enzyme |
|---|---|---|
| L-glutamic acid | 100 | 100 |
| L-tyrosine | 0 | 0 |
| L-methionine | 0 | 0 |
| L-phenylalanine | 0 | 0 |
| L-arginine | 0 | 0 |
| L-lysine | 0 | 0 |
| L-histidine | 0 | 0 |
| L-alanine | 0 | 0 |
| L-isoleucine | 0 | 0 |
| L-valine | 0 | 0 |
| L-threonine | 0 | 0 |
| L-serine | 0 | 0 |
| D-glutamic acid | 0 | 0 |
| methylamine | 0 | 0 |
| ethylamine | 0 | 0 |
| butylamine | 0 | 0 |
| propylamine | 0 | 0 |
| benzylamine | 0 | 0 |
| hydroxylamine | 0 | 0 |
| tyramine | 0 | 0 |

3. Enzyme action:

L-glutamic acid (0.5 μmole) is used as a substrate. The amounts of consumed oxygen, generated α-ketoglutaric acid, ammonia and hydrogen peroxide are measured. The results are shown in Table 4.

TABLE 4

| | A7700 enzyme | A8063 enzyme |
|---|---|---|
| added L-glutamic acid (μmole) | 0.50 | 0.50 |
| consumed oxygen (μmole) | 0.51 | 0.50 |
| generated α-ketoglutaric acid (μmole) | 0.48 | 0.49 |
| generated ammonia (μmole) | 0.48 | 0.49 |
| generated hydrogen peroxide (μmole) | 0.49 | 0.48 |

Consumed oxygen is measured by an ozygen electrode. Generated α-ketoglutaric acid is measured by the 2,4-dinitrophneylhydrazine method (*Kagaku No Ryoiki,* Suppl. 33, p. 99–104, "Spectrophotometry in Biochemistry", in Japanese). Ammonia is measured by the indophenol method [*J. Biol. Chem.,* 102, 499 (1933)]. Hydrogen peroxide is measured by the colorimetric assay method with peroxidase-4-aminoantipyrine-phenol.

Both enzymes catalyze a reaction which forms one mole of α-ketoglutaric acid, one mole of ammonia and one mole of hydrogen peroxide from one mole of L-glutamic acid, one mole of oxygen and one mole of water (reaction equation [I]):

$$\begin{array}{c}\text{COOH}\\|\\\text{CH}_2\\|\\\text{CH}_2\\|\\\text{H}-\text{C}-\text{NH}_2\\|\\\text{COOH}\end{array} + O_2 + H_2O \longrightarrow \begin{array}{c}\text{COOH}\\|\\\text{CH}_2\\|\\\text{CH}_2\\|\\\text{C}=\text{O}\\|\\\text{COOH}\end{array} + NH_3 + H_2O_2 \quad [I]$$

L-glutamic acid       α-ketoglutaric acid

4. Isoelectric point:

The isoelectric points of the A7700 enzyme and the A8063 enzyme are determined by the isoelectric focusing method using carrier ampholyte pH 3.5–6.0 (LKB Inc.). This isoelectric point of the A7700 enzyme is about pH 4.3 and that of the A8063 enzyme is about pH 4.1.

5. Km value:

The Km value of both enzymes against L-glutamic acid is about $5.6 \times 10^{-4}$M for the A7700 enzyme and about $1.1 \times 10^{-3}$M for the A8063 enzyme.

6. Optimum pH:

Glycine-HCl buffer (pH 2.5–4.5), dimethylglutarate-NaOH buffer (pH 4–7), phosphate buffer (pH 6–8), Tris-HCl buffer (pH 7–9) and glycine-NaOH buffer (pH 9–9.5) are used for determining the optimum pH of the enzyme.

Figure 2:
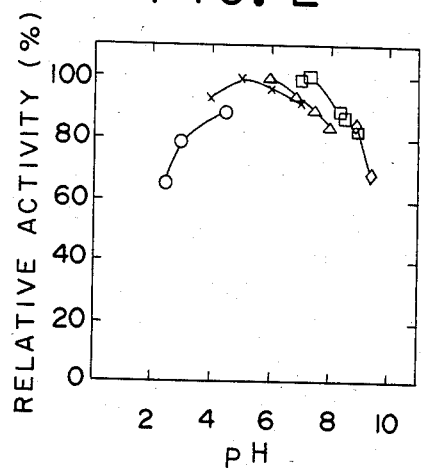
FIG. 2 is the optimum pH curve for the A8063 enzyme.

The results are shown in FIG. 1 for the A7700 enzyme and in FIG. 2 for the A8063 enzyme. In FIG. 1: : glycine-HCl buffer, x: dimethylglutarate-NaOH buffer, : phosphate buffer, : Tris-HCl buffer and : glycine-NaOH buffer. In FIG. 2: o: glycine-HCl buffer, x: dimethylglutarate-NaOH buffer, Δ: phosphate buffer, □: Tris-HCl buffer and : glycine-NaOH buffer. The optimum pH of both enzymes is pH 5–7.5.

7. Heat-stability:

Enzymes A7700 and A8063 dissolvedin 20 mM phosphate buffer (pH 7.0) are incubated at various temperatures for 10 mins., and immediately cooled in ice-cold water. Then the remaining activities are assayed.

Figure 3:
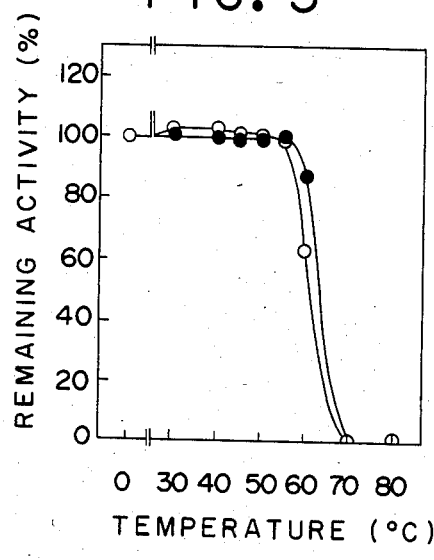
FIG. 3 is the heat stability curves of the A7700 and A8063 enzymes.

The results are shown in FIG. 3, wherein : A7700 enzyme and o: A8063 enzyme. Both enzymes are stable up to 55° C. and denatured at 70° C.

8. pH-stability:

pH-stability of the A7700 enzyme (FIG. 4) and the A8063 enzyme (FIG. 5) in various buffer solutions is measured.

The enzymes are dissolved in 40 mM concentration in each buffer solution, incubated at 37° C. for 60 minutes, and immediately cooled and the remaining activities are measured at each pH.

Figure 4:
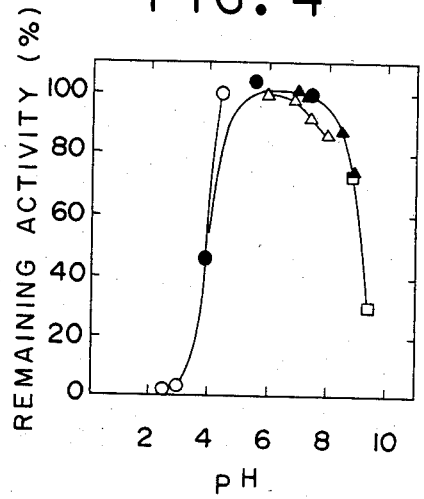
FIG. 4 is the pH stability curve of the A7700 enzyme.
Figure 5:
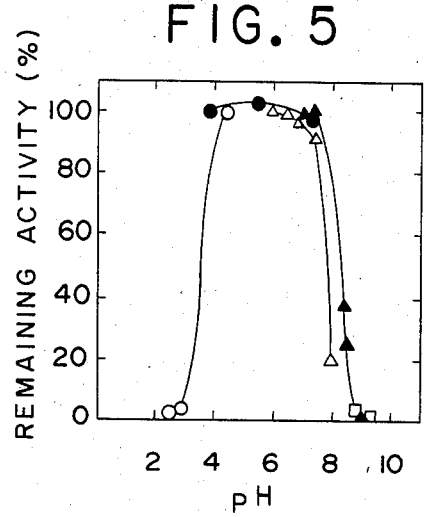
FIG. 5 is the pH stability curve of the A8063 enzyme.

The buffer solution for each pH is: glycine-HCl buffer (pH 2.5–4.5, o in FIGS. 4 and 5), dimethylglutarate-NaOH buffer (pH 4–7.5, ● in FIGS. 4 and 5), phosphate buffer (pH 6–8, Δ in FIGS. 4 and 5), Tris-HCl buffer (pH 7–9, ▲ in FIGS. 4 and 5) and glycine-NaOH buffer (pH 9–9.5, □ in FIGS. 4 and 5).

The A7700 enzyme is stable at pH 4.5–7.5 (FIG. 4) and the A8063 enzyme is stable at pH 4–7.5 (FIG. 5).

9. Effect of metal ions:

The effect of metal ions is shown in Table 5, in which ions other than $Cu^{++}$ show no effect on the enzymes.

TABLE 5

| metalic salt | concentration (mM) | Relative activity (%) A7700 enzyme | Relative activity (%) A8063 enzyme |
|---|---|---|---|
| control | — | 100 | 100 |
| $MnCl_2$ | 1.0 | 108.6 | 105.7 |
| $MgCl_2$ | 1.0 | 102.5 | 103.4 |
| $CaCl_2$ | 1.0 | 98.8 | 103.0 |
| $BaCl_2$ | 1.0 | 102.5 | 103.7 |
| $NiCl_2$ | 1.0 | 101.8 | 102.3 |
| $CoCl_2$ | 1.0 | 99.4 | 98.0 |
| $ZnCl_2$ | 1.0 | 106.1 | 110.7 |
| $CuCl_2$ | 1.0 | 50.3 | 62.1 |
| $FeCl_3$ | 1.0 | 109.2 | 103.0 |

10. Effect of surface active agents and other substances:

The effect of various substances on enzyme activity is shown in Table 6. The lack of effect of EDTA shows that both enzymes are not metalloenzymes. Also both enzymes are not inhibited by $NaN_3$ and KCN, and are not affected by FAD and FMN.

TABLE 6

| Additive | Concentration | Relative activity (%) A7700 | Relative activity (%) A8063 |
|---|---|---|---|
| Control | — | 100 | 100 |
| EDTA | 10 mM | 93.8 | 100.7 |
| $NaN_3$ | 10 mM | 101.4 | 102.6 |
| KCN | 10 mM | 103.5 | 102.9 |
| PCMB | 0.002% | 107.6 | 98.2 |
| FAD | 0.01 mM | 100.7 | 100.7 |
| FMN | 0.01 mM | 88.9 | 97.1 |
| Brij 35 | 0.5% | 65.3 | 86.9 |
| LBS | 0.1% | 131.9 | 110.2 |
| SDS | 0.1% | 106.3 | 93.1 |
| sodium cholate | 0.1% | 104.2 | 100.0 |
| Cation FB | 0.5% | 104.2 | 101.8 |
| CTACl | 0.1% | 98.6 | 94.2 |

As illustrated hereinabove, the A7700 enzyme and the A8063 enzyme have substrate specificity for L-glutamic acid and catalyze a reaction which forms one mole of α-ketoglutaric acid, one mole of ammonia and one mole of hydrogen peroxide from one mole of L-glutamic acid, one mole of oxygen and one mole of water, and are novel enzyme L-glutamic acid oxidases.

Such a novel enzyme L-glutamic acid oxidase can be used for the analysis of liquid samples containing L-glutamic acid by quantifying the amount of consumed oxygen, or generated α-ketoglutaric acid, ammonia or hydrogen peroxide.

A liquid sample to be assayed according to a method of the present invention can be a liquid sample containing L-glutamic acid. For example, samples of L-glutamic acid reagent, a fermentation liquor of L-glutamic acid, a beverage containing L-glutamic acid, and samples for assaying enzyme activity or determining the substrate in an enzymatic reaction system which forms or generates L-glutamic acid, or which consumes L-glutamic acid as a substrate, can be mentioned.

Examples of the said enzymatic reaction systems are as follows, wherein α-KG is α-ketoglutaric acid and L-GA is L-glutamic acid.

\*Glutamate-pyruvate transaminase (GPT):

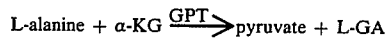
L-alanine + α-KG $\xrightarrow{GPT}$ pyruvate + L-GA

\*Glutamate-oxaloacetate transminase (GOT):

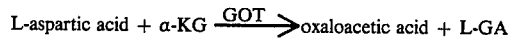
L-aspartic acid + α-KG $\xrightarrow{GOT}$ oxaloacetic acid + L-GA

\*Cysteine-aminotransferase (CATase):

L-cysteine + α-KG $\xrightarrow{CATase}$

β-mercaptopyruvic acid + L-GA

\*Tyrosine-aminotransferase (TATase):

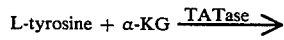
L-tyrosine + α-KG $\xrightarrow{TATase}$ p-hydroxyphenylpyruvic acid + L-GA \*Leucine aminotransferase (LATase):

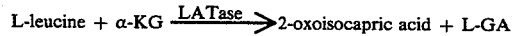
L-leucine + α-KG $\xrightarrow{LATase}$ 2-oxoisocapric acid + L-GA

\*Kynurenine aminotransferase (KATase):

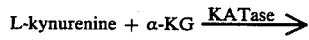
L-kynurenine + α-KG $\xrightarrow{KATase}$ o-aminobenzoylpyruvic acid + L-GA \*Aminobutylate aminotransferase (AATase):

4-aminobutanoic acid + α-KG $\xrightarrow{AATase}$ succinic semialdehyde + L-GA \*γ-glutamyl transpeptidase (γ-GPT):

L-glutamyl-X + L-GA $\xrightarrow{\gamma\text{-}GPT}$ glycyl-glycyl-X + L-GA (X: transfer group such as glutamyl-amino acid)

\*Glutamate racemase (GRase):

D-glutamic acid $\xrightarrow{GRase}$ L-GA

These enzyme reaction systems are illustrative only and do not limit the assay method of the present invention. Furthermore, assaying enzyme activity or the amount of substrate can be performed by quantifying the generated or liberated L-glutamic acid.

\*Amino acid actyltransferase (AAATase):

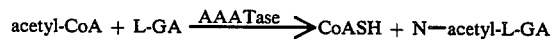
acetyl-CoA + L-GA $\xrightarrow{AAATase}$ CoASH + N—acetyl-L-GA

\*Glycine aminotransferase (GLATase):

glyoxalic acid + L-GA $\xrightarrow{GLATase}$ glycine + α-KG

-continued

*Glutamate decarboxylase (GDase):

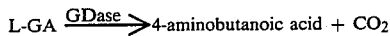

L-GA $\xrightarrow{\text{GDase}}$ 4-aminobutanoic acid + $CO_2$

*γ-glutamylcysteine synthetase (γ-GLCSase):

ATP + L-GA + L-cysteine $\xrightarrow{\gamma\text{-GLCSase}}$

γ-glutamyl-L-cysteine + ADP + Pi

The above enzymatic reaction systems are illustrative only and do not limit the samples to be assayed. In these enzymatic reactions, consuled L-glutamic acid as a substance is measured for assaying enzymatic activity.

In the assay method of the present invention, L-glutamic acid oxidase is subjected to reaction in the liquid sample containing L-glutamic acid. The L-glutamic acid oxidase can be in the form of an enzyme solution dissolved in a stable pH buffer, or an entrapped microcapsulated enzyme that preserves the enzyme without denaturation, or an immobilized enzyme form by means of e.g. covalent bonding with a resin, a polysaccharide or an inorganic glass.

The amount of L-glutamic acid oxidase can be varied depending on the amount of the liquid sample and the reaction time, and is preferably 2-10 units. A relatively high specific activity of the enzyme used is preferred; however, the highest purity of the enzyme is not always required.

The amount of the liquid sample containing L-glutamic acid is not limited, and is optionally prepared with or without dilution.

By these procedures, L-glutamic acid oxidase is caused to react with the said liquid sample, and the reaction mixture is incubated for a constant time and temperature, for example 5-20 minutes at about 37° C., to consume one mole of oxygen and to generate one mole of α-ketoglutaric acid, one mole of ammonia and one mole of hydrogen peroxide per one mole of L-glutamic acid.

The said oxygen, α-ketoglutaric acid, ammonia or hydrogen peroxide are quantified. Oxygen is preferably detected by an oxygen electrode. α-ketoglutaric acid is preferably detected by the colorimetric assay of hydrazine method with 2,4-dinitrophenylhydrazine (absorption at 415 nm or 530 nm). Ammonia can be detected by an ammonia electrode, or by an ion electrode after converting to ammonium ion, or by the indophenol method. Hydrogen peroxide is measured by a hydrogen peroxide electrode or by an indicator which reacts with hydrogen peroxide to form a detectable composition. Embodiments of such an indicator are a coloring indicator which undergoes visible changes, a fluorescent indicator which fluoresces under ultraviolet rays, or a luminescent composition. Examples of the coloring indicator are compositions comprising peroxidase active substances and pigment precursors. Horseradish peroxidase is preferably used, and the combination of an electron acceptor, a phenol derivative and an aniline derivative. Examples of electron acceptors are 4-aminoantipyrine, 4-amino-3-hydrazino-5-mercapto-1,2,4-triazole, 2-hydrazinobenzothiazole, 3-methyl-2-benzothiazolonehydrazone and 2-aminobenzothiazole. Examples of phenol derivatives or aniline derivatives are phenol, sodium p-hydroxybenzoic acid, p-chlorophenol, 2,4,-dichlorophenol, 4,6-dichloro-o-cresol, 2,4-dibromophenol, N,N-dimethylaniline, N,N-diethylaniline, N,N-dimethyl-m-toluidine, N,N-dimethyl-m-toluidine, N,N-dimethyl-m-methoxytoluidine, N,N-diethanol-m-toluidine, 3-methyl-N-ethyl-N-hydroxyethylaniline, N-ethyl-N-(3-methylphenyl)-N-acetylethylenediamine, sodium N-ethyl-N-hydroxyethyl-m-toluidine, N-ethyl-N-sulfopropyl-m-toluidine, sodium N-ethyl-N-(2-hydroxy-3-sulfopropyl)-m-toluidine or m-acetoamino-N,N-diethylaniline. A coloring complex of 4-aminoantipyrine and a phenol derivative can be measured at 500-520 nm and a complex of 4-aminoantipyrine and aniline derivatives can be measured at 535-580 nm. Examples of fluorescent substrates in fluorometry and luminometry are bis(2,4,6-trichlorophenol)oxalate, phenylthiohydantoin, homovanillic acid, 4-hydroxyphenylacetic acid, vanillylamine, 3-methoxythiramine, phloretin, hordenine, luminolmonoanion, lucigenin or waffin. These substances can optionally be used together with electron acceptors and peroxidase active substances for the determination of hydrogen peroxide. In the indicator reagent which changes to a detectable substance by reacting with hydrogen peroxide, for example, the amount of peroxidase used is more than 0.1 unit per one test, preferably 1-10 units.

Since the electron acceptors such as 4-aminoantipyrine or the phenol derivatives or aniline derivatives are reacted and consumed in the amount of one mole thereof, as compared with two moles of hydrogen peroxide, these substances should be used in excess of the amount of generated hydrogen peroxide, preferably in more than five molar excess of the amount of hydrogen peroxide.

These reagents are preferably mixed and prepared in solution, or mixed with a solution of L-glutamic acid oxidase, or can be prepared in a solid phase which is layered on a synthetic resin film or filter paper. Furthermore, an enzyme electrode attached to the immobilized L-glutamic acid oxidase can preferably be used as an electric means of detection.

The amount of L-glutamic acid in a sample can be calculated from the calibration curve of the thus-quantified amount of oxygen, α-ketoglutaric acid, ammonia or hydrogen peroxide.

The following examples illustrate the present invention but are not to be construed as limiting:

EXAMPLE 1

An aqueous medium (100 ml, pH 7.0) comprising peptone 0.5%, meat extract 0.3%, yeast extract 0.1% and malt extract 0.5% in a 500 ml Erlenmeyer flask was sterilized at 120° C. for 20 mins. A four-days culture of Streptomyces sp. A7700 FERM-P 6241 was inoculated therein and the mixture was cultured at 26° C. for 4 days. The cultured cells obtained by centrifugation were ground with quartz sand in a mortar. The enzyme was extracted by adding 20 mM phosphate buffer (pH 7.0) and the extract was collected. The L-glutamic acid oxidase in the cultured broth was calculated as 0.13 u/ml.

EXAMPLE 2

In Example 1, Streptomyces sp. A7700 FERM P-6241 was replaced by Streptomyces sp. A8063 FERM P-6242. The L-glutamic acid oxidase in the cultured broth was calculated as 0.59 u/ml.

EXAMPLE 3

Two 500 ml Erlenmeyer flasks each containing 100 ml of medium comprising peptone 0.5%, meat extract 0.3%, yeast extract 0.1% and malt extract 0.5% were sterilized at 120PC for 20 mins. Streptomyces sp. A8063 FERM P-6242 was inoculated in the said medium and the mixture was cultured at 26° C. for 3 days.

These seed cultures (200 ml) were inoculated into an aqueous medium (20 lit., pH 7.0) comprising peptone 0.5%, meat extract 0.3%, yeast extract 0.1% and malt extract 0.5% in a 30-liter fermenter which was previously sterilized at 120° C. for 20 mins., and the mixture was cultured at 26° C., with aeration at 20 l/min., and 300 rpm agitation, for 96 hours. The cultured broth was centrifuged at 5000 rpm for 5 mins. to obtain the cultured cells. The cells were suspended in 20 mM phosphate buffer (3 lit., pH 7.0) and ground with a Dyno-Mill (trademark, Willy A. Bachofen Manufact. Engineers, Switzerland). The ground cells were centrifuged at 5000 rpm for 15 mins. to obtain a supernatant solution of 2.82 lit. (11200 units).

Ammonium sulfate was added to the supernatant solution and the fractions were collected which were precipitated at 0.4–0.53 saturation. The precipitate, dissolved in 20 mM phosphate buffer (pH 7.0), was packed into a cellophane tube and dialyzed against 20 mM phosphate buffer (pH 7.0, 12 lit.) for 20 mins. The dialyzate was charged on a column (50×400 m/m) packed with DEAE-sepharose CL-6B, and eluted with a linear gradient of 0–0.7M KCl in 20 mM phosphate buffer (pH 7.0). The fractions eluted with 0.5M KCl (130 ml, 6690 units) were dialyzed with a cellophane tube against 6 lit. of 20 mM phosphate buffer for 18 hours. The dialyzate was concentrated in vacuo (to 15 ml). The concentrate was charged on a column of Sepharose CL-6B, and eluted with 10 mM phosphate buffer (pH 7.0) to obtain an eluate (80 ml, 5900 units).

The eluate was concentrated by ultrafiltration up to 8 ml, and again charged on a column of Sepharose CL-6B, then eluted by the same buffer solution hereinabove to obtain the eluate (60 ml, 4890 units). The eluate was lyophilized to yield L-glutamic acid oxidase (78.0 mg, 58.2 U/mg, 4595 units).

EXAMPLE 4

An aqueous medium (pH 7.0, 20 lit.) comprising peptone 0.5%, meat extract 0.3%, yeast extract 0.1% and malt extract 0.5% was introduced into a 30 lit. jar fermenter and sterilized at 120° C. for 20 mins. A seed culture (200 ml) of Streptomyces sp. A7700 FERM P-6241 cultured for 3 days in the same medium was inoculated into the above medium and submerged cultured at 26° C. for 96 hours, with aseptic aeration of 20 lit./min. and 300 rpm agitation. The cultured broth was separated centrifugally at 5000 rpm for 5 mins. and the obtained cells were suspended in 20 mM phosphate buffer (pH 7.0, 3 lit.), then disrupted with a Dyno-Mill. The disrupted cells were centrifuged at 5000 rpm for 15 mins. to obtain a supernatant solution (2.84 lit., 2950 units). Ammonium sulfate was added thereto and the precipitate was collected at 0.47–0.61 saturation. The precipitate was dissolved in a 20 mM phosphate buffer (pH 7.0) and dialyzed in a cellophane tube against 20 mM phosphate buffer (pH 7.0) for 20 hours. The dialyzate was charged on a column of DEAE-sepharose CL-6B and eluted by linear gradient elution with 0–0.7M KCl in 20 mM phosphate buffer (pH 7.0). The eluate at about 0.5M KCl was collected, dialyzed through a cellophane tube against 10 mM phosphate buffer (pH 7.0) for 18 hours, and concentrated. Then the dialyzate was charged on a column of Sepharose CL-6B and the eluate was concentrated. The Sepharose CL-6B column chromatography was repeated and the eluate was lyophilized to obtain a powder of L-glutamic acid oxidase (22.0 mg, 49.5 units/mg, 1080 units).

EXAMPLE 5

[Quantitative determination of L-glutamic acid]:
40 mM phosphate buffer (pH 6.5)
0.03% 4-aminoantipyrine
0.04% N,N-dimethyl-m-toluidine
2 u/ml peroxidase
2 u/ml L-glutamic acid oxidase The reaction mixture (3.0 ml) hereinabove was mixed with 1/1, ¾, ½, ¼, 1/5 and 1/10 diluted 10 mM L-glutamic acid solutions (50 μl each), respectively, and the mixtures were incubated at 37° C. for 10 mins. After incubation, each reaction mixture was measured colorimetrically at 545 nm.

Figure 6:
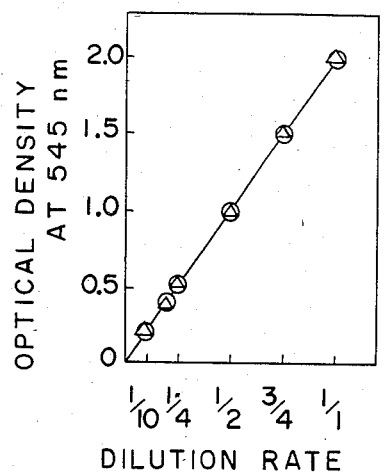
FIG. 6 is the calibration curve of L-glutamic acid using A7700 and A8063 enzyme.

The results are shown in FIG. 6. In that figure, o shows L-glutamic acid oxidase obtained in Example 3, and Δ shows L-glutamic acid oxidase obtained in Example 4. The results of both enzymes are quite identical with each other and good linearity between the amount of L-glutamic acid and the absorption ratio is obtained.

The following examples are performed by using L-glutamic acid oxidase obtained in Example 3.

EXAMPLE 6

[Assay of serum GPT]:

| | |
|---|---|
| N,N—diethyl-m-toluidine | 3 mM |
| 4-aminoantipyrine | 1.5 mM |
| peroxidase | 5 units/ml |
| L-alanine | 200 mM |
| α-ketoglutaric acid | 10 mM |
| Tris-HCl buffer (pH 7.5) | 50 mM |
| L-glutamic acid oxidase | 6 units/ml |

Figure 7:
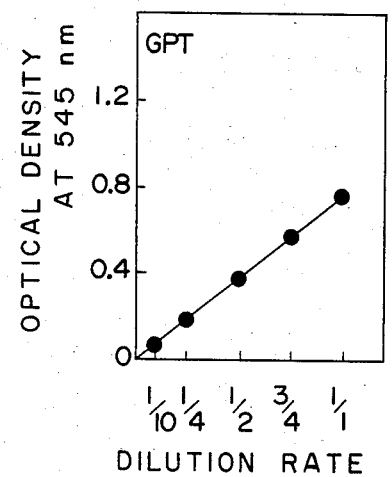
FIG. 7 is the calibration curve of serum GPT.

The above aqueous reaction mixture (1.0 ml) was collected in small test tubes and preincubated at 37° C. Serum (50 μl, 1/1, ¾, ½, ¼, 1/10 dilution, respectively) were added and incubated for exactly 20 mins. at 37° C. 0.1M McIlvain buffer (pH 5.5, 2.0 ml) was added to each and each was colorimetrically measured at 545 nm. As a control, the above reaction mixture was used, but from which L-alanine was removed. The results are shown in FIG. 7, from which it can be seen that serum GPT can be assayed exactly.

EXAMPLE 7

[Assay of serum GOT]:

| | |
|---|---|
| N,N—diethyl-m-toluidine | 3 mM |
| 4-aminoantipyrine | 1.5 mM |
| peroxidase | 5 u/ml |
| L-aspartic acid | 200 mM |
| α-ketoglutaric acid | 10 mM |
| Tris-HCl buffer (pH 7.5) | 50 mM |
| L-glutamic acid oxidase | 6 u/ml |

An aqueous reaction mixture (1.0 ml) of the above composition was collected in small test tubes and preincubated at 37° C. Serum (1/1, ¾, ½, ¼, 1/10 dilution) (50 μl each) was added therein and incubated at 37° C. for exactly 20 mins. 0.1M McIlvain buffer (pH 5.5, 2.0 ml) was added and the mixture was colorimetrically measured at 545 nm. A reaction mixture with L-aspartic acid omitted from the above mixture is used as a control.

Figure 8:
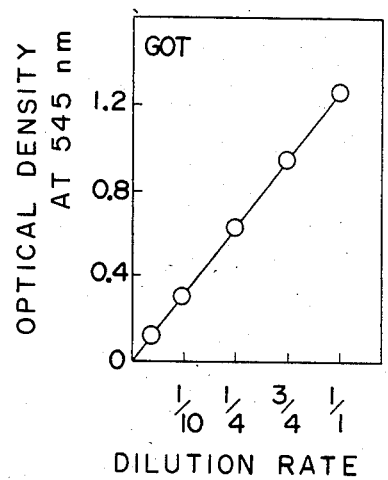
FIG. 8 is the calibration curve of serum GOT.

The results are shown in FIG. 8, from which it can be seen that serum GOT can be assayed exactly.

EXAMPLE 8

[Serum GPT assay]:

[Reagent I]

| | |
|---|---|
| N—ethyl-N—sulfopropyl-m-toluidine | 3 nM |
| peroxidase | 5 u/ml |
| L-alanine | 200 mM |
| α-ketoglutaric acid | 10 mM |
| Tris-HCl buffer (pH 7.5) | 50 mM |
| L-glutamic acid oxidase | 5 u/ml |
| ascorbic acid oxidase | 5 u/ml |

[Reagent II]

| | |
|---|---|
| 4-aminoantipyrine | 15 mM |

Reagent I (1 ml) was introduced into a quartz cell. Serum (50 μl) was added thereto and the mixture was incubated at 37° C. for 5 mins. Reagent II (0.1 ml), preincubated at 37° C., was added thereto and the mixture was incubated at 37° C. for various times, then colorimetrically measured at 550 nm.

Figure 9:
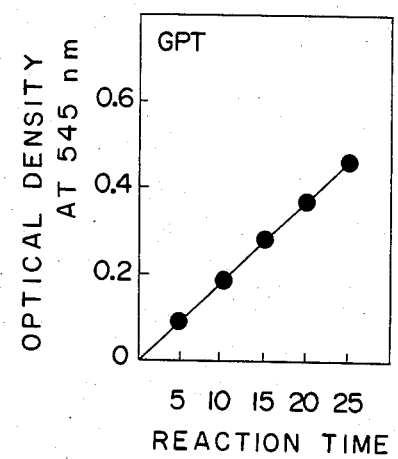
FIG. 9 is the calibration curve of serum GPT using two reagents.

The results are shown in FIG. 9, from which no lag time is found in the serum GPT assay and a good linear calibration curve crossing the origin is obtained.

In this assay method, non-specific reaction and lag time are deleted in the first step of the reaction and hence no control assay is required.

EXAMPLE 9

[Serum GOT assay]:

[Reagent I]

| | |
|---|---|
| N—ethyl-N—sulfopropyl-m-toluidine | 3 mM |
| peroxidase | 5 u/ml |
| L-aspartic acid | 200 mM |
| α-ketoglutaric acid | 10 mM |
| Tris-HCl buffer (pH 7.5) | 50 mM |
| L-glutamic acid oxidase | 5 u/ml |
| ascorbic acid oxidase | 5 u/ml |

[Reagent II]

| | |
|---|---|
| 4-aminoantipyrine | 15 mM |

Reagent I (1.0 ml) was introduced into a quartz cell and the serum (50 μl) was added thereto, then the mixture was incubated at 37° C. for 5 mins. Reagent II (0.1 ml), preincubated at 37° C., was added to the reaction mixture, which was incubated at 37° C. for various times, then colorimetrically measured at 550 nm.

Figure 10:
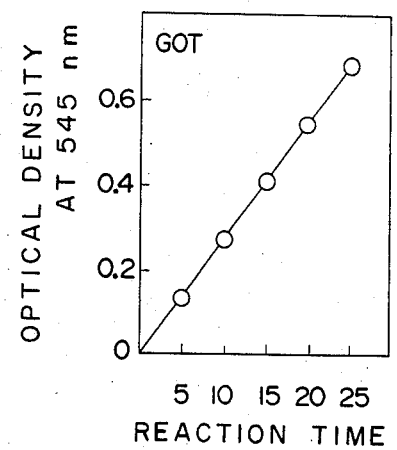
FIG. 10 is the calibration curve of serum GOT using two reagents.

The results are shown in FIG. 10 in which no lag time is observed and no control experiment is required. As shown in FIG. 10, a good linear calibration curve for the assay of GOT crossing the origin is obtained.

EXAMPLE 10

In Example 8, the same reagents I and II were used but the serum sample was replaced by 40 serum specimens (each 50 μl) to assay serum GPT activity.

Also the same specimens were assayed by using a prior known method [UV-method, Wako Pure Chem. Co., assay kit GPT-UV WAKO].

Figure 11:
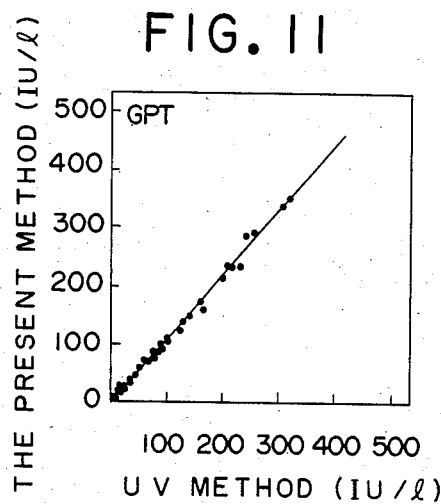
FIG. 11 is the correlation curve of serum GPT activity.

The correlation calculated from the results of both methods is as follows:

$\gamma = 0.998$ $y = 1.03x + 1.6$ wherein good correlation is obtained. The correlation curve is shown in FIG. 11.

EXAMPLE 11

Serum GOT activity is assayed according to a method of Example 9 with 40 serum specimens (each 50 μl).

The same specimens were assayed by using a prior known GOT assay method [UV-method, Wako Pure Chem. Co., kit GOT-UV WAKO].

Figure 12:
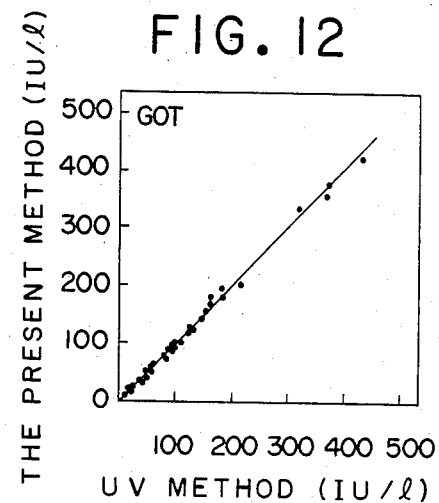
FIG. 12 is the correlation curve of serum GOT activity.

The correlation of both test results is:

$\gamma = 0.997$ $v - 1.01x + 1.1$ wherein a good correlation curve is obtained as shwon in FIG. 12.

What is claimed is:

1. L-glutamic acid oxidase having the following biochemical properties:
   (a) substrate specificity: L-glutamic acid,
   (b) enzyme action: catalyzes a reaction which forms one mole of α-ketoglutaric acid, one mole of ammonia and one mole of hydrogen peroxide from one mole of L-glutamic acid, one mole of oxygen and one mole of water, as follows:

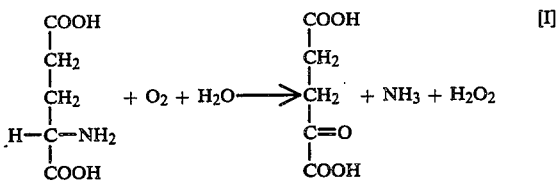

2. L-glutamic acid oxidase according to claim 1, which has
   (i) an isoelectric point at about pH 4.3 (measured by carrier ampholyte pH 3.5–6.0),
   (ii) a Km for L-glutamate of about $5.6 \times 10^{-4}$M,
   (iii) an optimum pH of about pH 5–7.5,
   (iv) heat stability up to about 55° C., and
   (v) pH stability of about pH 4.5–7.5.

3. L-glutamic acid oxidase according to claim 1, which has
   (i) an isoelectric point at about pH 4.1 (measured by carrier ampholyte pH 3.5–6.0),
   (ii) a Km for L-glutamate of about $1.1 \times 10^{-3}$M,
   (iii) an optimum pH of about pH 5–7.5,
   (iv) heat stability up to about 55° C., and
   (v) pH stability of about pH 4–7.5.

4. A process for the production of L-glutamic acid oxidase as claimed in claim 1, which comprises culturing L-glutamic acid oxidase producing microorganisms belonging to genus Streptomyces and selected from the group consisting of Streptomyces sp. A7700 FERM P-6241 and Streptomyces sp. A8063 FERM P-6242, in a nutrient medium and isolating the thus-produced L-glutamic acid oxidase.

5. A process according to claim 4, wherein the L-glutamic acid oxidase producing microorganisms belonging to genus Streptomyces is Streptomyces sp. A7700 FERM P-6241.

6. A process according to claim 4, wherein the L-glutamic acid oxidase producing microorganisms belonging to genus Streptomyces is Streptomyces sp. A8063 FERM P-6242.

7. A method for detecting L-glutamic acid or L-glutamate, comprising contacting in an aqueous medium a sample containing L-glutamic acid for analysis and L-glutamic acid oxidase which has substrate specificity for L-glutamic acid, and which catalyzes a reaction which forms one mole of α-ketoglutaric acid, one mole of ammonia and one mole of hydrogen peroxide from one mole of glutamic acid, one mole of oxygen and one mole of water, and quantitatively determining consumed oxygen or generated α-ketoglutaric acid, ammonia or hydrogen peroxide.

8. A method according to claim 7, wherein the quantitative determination of hydrogen peroxide is performed by an indicator that undergoes a detectable change upon reaction with hydrogen peroxide.

9. A method according to claim 8, wherein the said indicator is a coloring reagent, a fluorescent reagent or a luminescent reagent.

10. A method according to claim 7, wherein said L-glutamic acid oxidase is an enzyme obtained from L-glutamic acid oxidase producing microorganisms belonging to genus Streptomyces.

11. A method according to claim 7, wherein said sample containing L-glutamic acid is a liquid sample of an enzyme reaction system which liberates or generates L-glutamic acid.

12. A method according to claim 11, wherein the said liquid sample of an enzyme reaction system is a sample for assaying glutamate-pyruvate transaminase activity.

13. A method according to claim 11, wherein the said liquid sample of an enzyme reaction system is a sample for assaying glutamate-oxaloacetate transaminase activity.

14. A method according to claim 11, wherein the said liquid sample of an enzyme reaction system is a sample for assaying peptidase activity.

* * * * *